US009996929B2

(12) United States Patent
Waschbuesch et al.

(10) Patent No.: US 9,996,929 B2
(45) Date of Patent: Jun. 12, 2018

(54) VISUALIZATION OF DEFORMATIONS USING COLOR OVERLAYS

(75) Inventors: Michael Waschbuesch, Rheinfelden (CH); Lasse Toimela, Baden-Daettwil (CH); Armel C. Rosselet, Baden (CH)

(73) Assignee: Varian Medical Systems International AG, Zug (CH)

( * ) Notice: Subject to any disclaimer, the term of this patent is extended or adjusted under 35 U.S.C. 154(b) by 335 days.

(21) Appl. No.: 12/925,663

(22) Filed: Oct. 27, 2010

(65) Prior Publication Data

US 2012/0105430 A1 May 3, 2012

(51) Int. Cl.
*G06K 9/00* (2006.01)
*G06T 7/00* (2017.01)
*A61B 5/00* (2006.01)
*A61B 6/00* (2006.01)
*A61B 8/00* (2006.01)

(52) U.S. Cl.
CPC .......... *G06T 7/0016* (2013.01); *A61B 5/7425* (2013.01); *A61B 6/463* (2013.01); *A61B 8/463* (2013.01); *G06T 2200/24* (2013.01); *G06T 2207/10072* (2013.01); *G06T 2207/10132* (2013.01); *G06T 2207/30004* (2013.01)

(58) Field of Classification Search
CPC ... A61B 5/7425; A61B 5/0033; A61B 5/0035; A61B 5/0037; A61B 5/0042; A61B 5/0044; A61B 6/463; A61B 8/463; G06T 2200/24; G06T 2207/10072
See application file for complete search history.

(56) References Cited

U.S. PATENT DOCUMENTS

| | | | | |
|---|---|---|---|---|
| 5,531,227 | A | * | 7/1996 | Schneider ..................... 600/425 |
| 6,304,670 | B1 | | 10/2001 | Berestov |
| 2005/0238253 | A1 | * | 10/2005 | Behrenbruch et al. ....... 382/294 |
| 2008/0050043 | A1 | * | 2/2008 | Hermosillo Valadez et al. ............................ 382/294 |

(Continued)

OTHER PUBLICATIONS

Riddle et al., "Quantifying cerebral changes in adolescence with MRI and deformation based morphometry", Jul. 29, 2008, Journal of Magnetic Resonance Imaging, vol. 28, iss. 2, p. 320-326.*

(Continued)

*Primary Examiner* — Vincent Rudolph
*Assistant Examiner* — Timothy Choi
(74) *Attorney, Agent, or Firm* — Edward J. Radlo; Radlo IP Law Group

(57) ABSTRACT

Computer-implemented methods and apparati for graphically displaying deformations, said deformations defined by comparing a first image of an object (1) with a second image of the same or a different object (1). A method embodiment of the present invention comprises the steps of scanning an object (1) twice to produce first and second images; tabulating deformations and converting said tabulated deformations into a scalar property over a preselected range; quantizing the range into a set of discrete quantization intervals; assigning a unique color out of a discrete or quasi-continuous set of colors to each quantization interval to produce a color overlay; and simultaneously displaying the color overlay and a representation of at least one of the first and second images, whereby said deformations are readily viewable in color.

2 Claims, 5 Drawing Sheets
(3 of 5 Drawing Sheet(s) Filed in Color)

(56) References Cited

U.S. PATENT DOCUMENTS

2011/0317887 A1 12/2011 Huber et al.
2011/0317896 A1 12/2011 Huber et al.

OTHER PUBLICATIONS

Lian et al., "Mappning of the prostate in endocrectal coil-based MRI/MR deformable registration and validation study", Oct. 28, 2004, The International Journal of Medical Physics Research and Practice, vol. 31, iss. 11, p. 3087-3094.*
Ledesma-Carbayo et al., "Spatio-temporal nonrigid registration for ultrasound cardiac motion estimation", Sep. 2005, IEEE Transactions on Medical Imaging, vol. 24, iss. 9, p. 1113-1126.*
Nagel et al., "Noninvasive Diagnosis of Ischemia-Induced Wall Motion Abnormalities With the Use of High-Dose Dobutamine Stress MRI Comparison With Dobutamine Stress Echocardiography", 1999, Circulation, p. 763-770.*
Montagnat et al., "Space and Time Shape Constrained Deformable Surfaces for 4D Medical Image Segmentation", 2000, Medical Image Computing and Computer-Assisted Intervention Lecture Notes in Computer Science, vol. 1935/2000, p. 196-205.*
Cevidanes et al., "3D Morphometric Changes 1 Year After Jaw Surgery", Apr. 15, 2007, 4th IEEE International Symposium on Biomedical Imaging: From Nano to Macro, p. 1332-1335.*
Veeser et al., "Multiresolution image registration for two-dimensional gel electrophoresis", 2001, Proteomics, vol. 1, p. 856-870.*
Lee et al., "Multimodal and three-dimensional imaging of prostate cancer", Sep. 2005, Computerized Medical Imaging and Graphics, vol. 29, iss. 6, p. 477-486.*
Collins et al., "Automatic 3-D model-based neuroanatomical segmentation", 1995, Human Brain Mapping, vol. 3, iss. 3, p. 190-208.*
Gerardo Hermosillo Valadez, "Variational Methods for Multimodal Image Matching", May 2002, Universite de Nice—Sophia Antipolis, p. 167-169.*
Specht et al., "Visualizing shape transformation between chimpanzee and human braincases", Jun. 9, 2007, Springer-Verlag, The Visual Computer, vol. 23, iss. 9, p. 743-751.*
MeshValmet, "MeshValmet: Validation Metric for Meshes", Sep. 23, 2015, NITRC, <https://www.nitrc.org/projects/meshvalmet>.*
Forsberg et al., "Adaptive Anisotropic Regularization of Deformation Fields for Non-Rigid Registration", Proceedings of the SSBA Symposium on Image Analysis, Uppsala, Sweden, Mar. 2010.
"TrueD Deformable Registration, Algorithm Description and Results Interpretation", 2007 Siemens Medical Solutions USA, Inc.
Thirion, J.-P., "Image matching as a diffusion process: an analogy with Maxwell's demons," Medical Image Analysis (1998) vol. 2, No. 3, pp. 243-260.
Dawant, B.M. et al., "Automatic 3-D segmentation of internal structures of the head in MR images using a combination of similarity and free-form transformations. I. Methodology and validation on normal subjects," Medical Imaging, IEEE Transactions on (sic) (vol. 18, Issue 10), Oct. 1999, Abstract, 2 pages., U.S.A.
Dawant, B.M. et al., "Automatic 3-D segmentation of internal structures of the head in MR images using a combination of similarity and free-form transformations," Part of the SPIE Conference on Image Processing, San Diego, California, Feb. 1998, SPIE vol. 3338, 0277-786X/98, pp. 545-554.
Insight Segmentation and Registration Toolkit, sponsored by the National Library of Medicine. U.S.A., http://www.itk.org, Accessed Jun. 4, 2013, 5 pages.

* cited by examiner

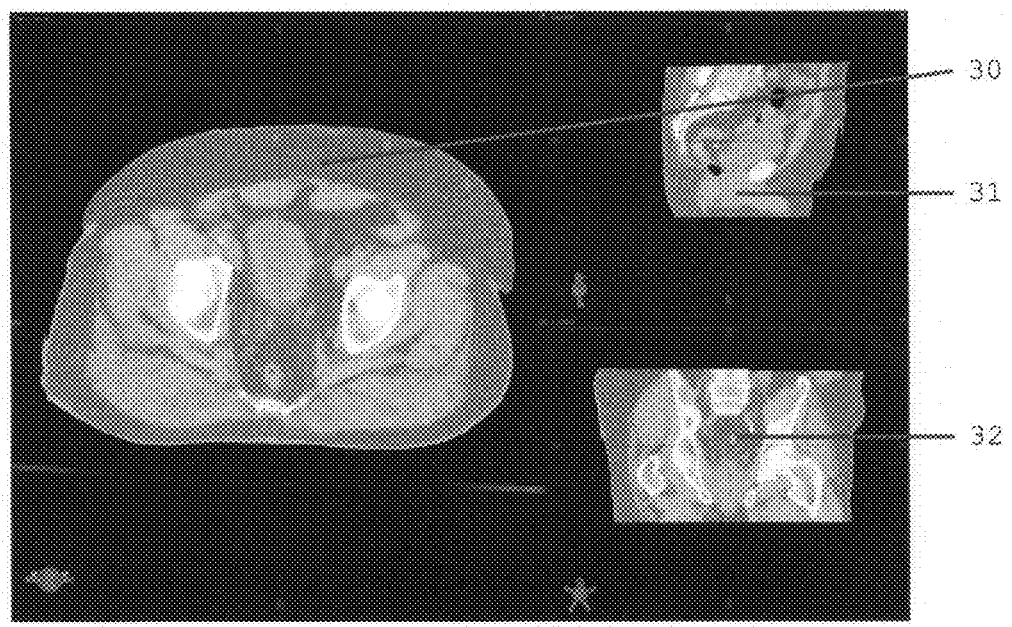
Fig. 3 - PRIOR ART
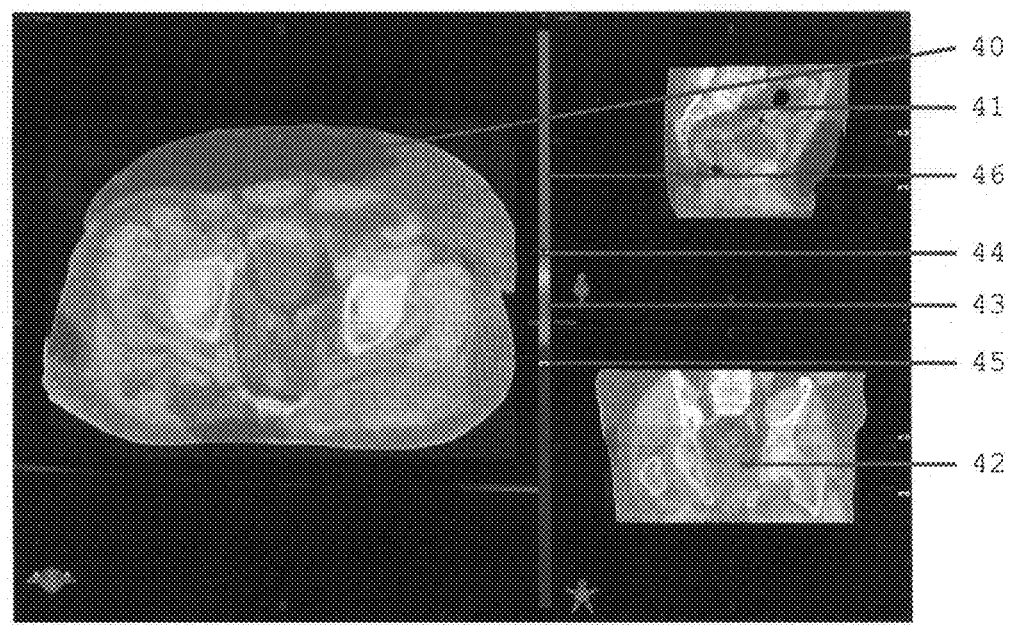
Fig. 4

VISUALIZATION OF DEFORMATIONS USING COLOR OVERLAYS

RELATED PATENT APPLICATIONS

Commonly-owned U.S. patent application Ser. No. 12/821,977 filed Jun. 23, 2010, entitled "Mechanism for Dynamically Propagating Real-Time Alterations of Medical Images" and Ser. No. 12/821,985 filed Jun. 23, 2010, entitled "Mechanism for Advanced Structure Generation and Editing" are hereby incorporated by reference in their entireties into the present patent application.

TECHNICAL FIELD

This invention pertains to the field of computer-implemented methods and apparati for displaying results of imaging, such as the imaging of deformations in a human body that is being treated with adaptive radiation therapy.

BACKGROUND ART

In adaptive radiation therapy, treatments are changed (adapted) on a periodic basis to account for changes in the patient's anatomy. For the detection of anatomical changes, an image is periodically acquired using a tomographic technique. The new (registered) images are compared to the initial (reference) image that was used for the patient's initial treatment plan. Deviations from the reference image caused by, e.g., tumor shrinkage or organ movement, are then used to adapt the course of treatment undertaken by the attending physicians.

In order to compare two such images, correspondences are normally established by calculation of a deformation map. The deformation map contains, for each pixel in the registered image, a three-dimensional vector that describes how this pixel has moved between the reference image and the registered image. Thus, the deformation map contains complete information about changes in geometry in the section of interest within the patient's anatomy. The deformation map typically comprises a vector field. However, the internal storage implementation of the deformation map in the associated computer can differ from a vector field representation, in which case said implementation can be converted to a vector field automatically or upon demand of the user.

In existing systems, volumetric (three-dimensional) patient images are usually visualized by displaying all pixels at the intersections of the 3D volume with arbitrarily-oriented user-definable two-dimensional slice planes. Pairs of registered images are then displayed, by first deforming the reference image into the space of the registered image using the deformation map, and then by displaying these slices either as side-by-side comparisons or as blended overlay images. While such visualization techniques can serve to compare both images, they do not provide any information about particular local properties of the deformations. The user can see only whether or not the images match, but cannot observe the degree of deformation at particular places.

These issues are addressed by the present invention, which provides novel techniques for visualization of deformations, e.g., by using color overlays.

DISCLOSURE OF INVENTION

Computer-implemented methods and apparati for graphically displaying deformations, said deformations defined by comparing a first image of an object (1) with a second image of the same or a different object (1). A method embodiment of the present invention comprises the steps of scanning an object (1) twice to produce first and second images; tabulating deformations and converting said tabulated deformations into a scalar property over a preselected range; quantizing the range into a set of discrete quantization intervals; assigning a unique color out of a discrete or quasi-continuous set of colors to each quantization interval to produce a color overlay; and simultaneously displaying the color overlay and a representation of at least one of the first and second images, whereby said deformations are readily viewable in color.

BRIEF DESCRIPTION OF THE DRAWINGS

The file of this patent or application contains at least one drawing executed in color. Copies of this patent or patent application publication with color drawings will be provided by the United States Patent and Trademark Office upon request and upon payment of the necessary fee.

Pertinent features of the present invention are disclosed in the following specification, reference being had to the accompanying drawings, in which:

FIG. 3 is a screen shot showing results of the prior art in which deformed images 30, 31, 32 are displayed.

FIG. 4 is a screen shot showing results of a first embodiment of the present invention in which deformed images 40, 41, 42 are displayed along with superimposed color overlays.

DETAILED DESCRIPTION OF THE PREFERRED EMBODIMENTS

Figure 1:
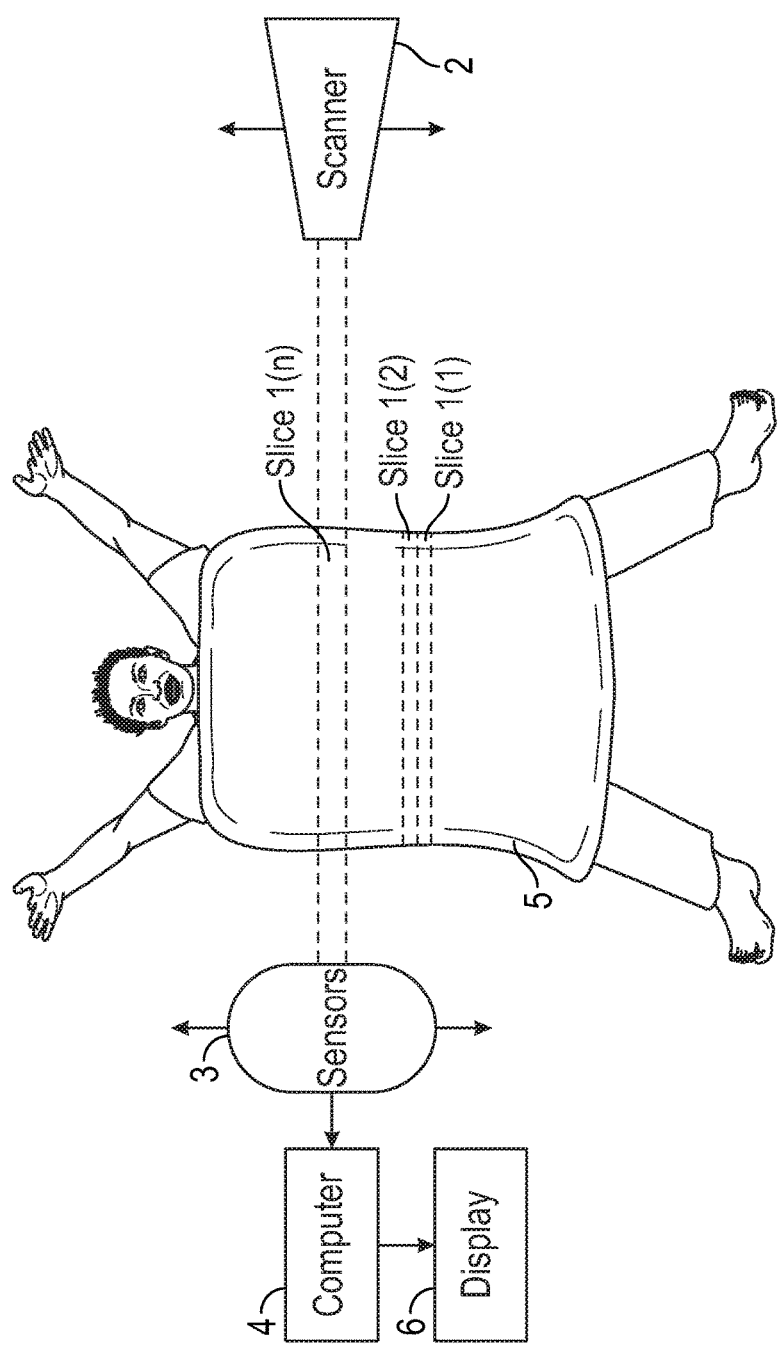
FIG. 1 is an apparatus diagram showing tomographic apparatus used by the prior art and by the present invention.

FIG. 1 illustrates apparatus used by the prior art and by the present invention. A scanner 2 emits radiation towards an object 5 to be imaged. Object 5 can be a human body or a portion of a human body. Object 5 can also be an inanimate object or an animal other than a human. Scanner 2 can be any type of scanner, such as a computerized tomographic (CT) scanner, a cone beam computerized tomographic (CBCT) scanner, a magnetic resonance imaging (MRI) scanner, a positron emission tomographic (PET) scanner, or an ultrasound scanner. One or more sensors 3 record the radiation after it has passed though object 5. This information is sent to computer 4, which processes the information and formats it for display on display 6.

Scanner 2 and sensors 3 may rotate in fixed relationship to each other about a certain axis, e.g., an axis that is parallel to the spine of the human being 5 that is illustrated in FIG. 1. Scanner 2 and sensors 3 may also, in fixed relationship to each other, perform stepwise scans by varying the plane of rotation in discrete steps. By this means, a plurality of thin slices 1 within object 5 can be imaged. Computer 4 then takes all of the information from the slices 1, and creates a three-dimensional volume containing information from all of the slices 1. The slices 1 each have a finite thickness, as defined by the underlying physics, and by the geometry of the imaging apparatus 2, 3 and an associated collimator (not shown).

Figure 2:
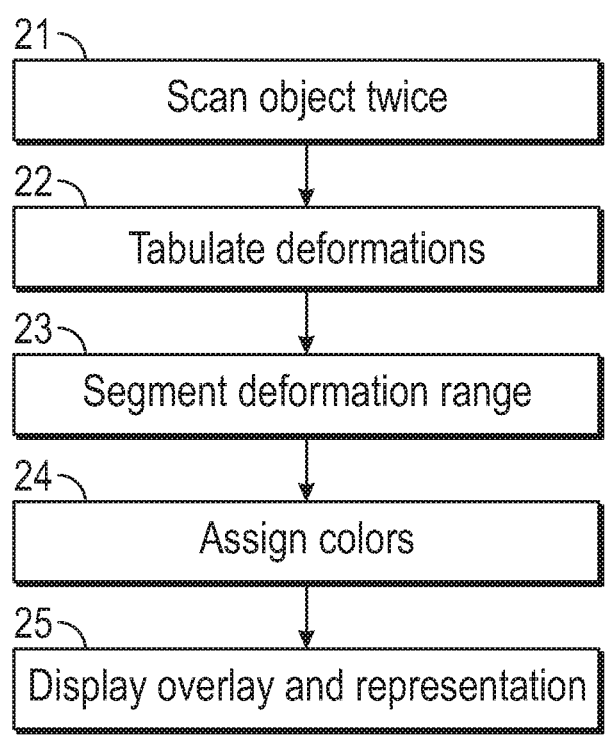
FIG. 2 is a high-level block diagram showing method embodiments of the present invention.

Various method embodiments of the present invention will now be described in conjunction with an elaboration of FIG. 2.

In step 21, object 5 is scanned twice. This produces first and second images. The first and second images can be produced by the same scanner 2. Alternatively, the images can be produced by the same type of scanner 2 but not the identical scanner 2, or by different types of scanners 2.

In one embodiment, the first image is a view of the object 5 scanned at a first time, and the second image is a view of the object 5 scanned at a second time that is subsequent to the first time. In another embodiment, the first and second images are two-dimensional images each taken at a single time (e.g., by two different scanners). In another embodiment, the first and second images are two-dimensional videos imaged over a preselected amount of time. In an alternative embodiment, the first and second images are three-dimensional videos imaged over a preselected amount of time. In another embodiment, the first and second images are different frames of a two-dimensional or three-dimensional video. In an alternative embodiment, the first and second images are two- or three-dimensional images or videos, not of the same but of different objects.

In step 22, computer 4 tabulates deformations of a scalar property over a preselected range. As used in the present specification including claims, "deformations" means geometrical changes in portions of object 5 when one compares image 1 to image 2. For example, in the embodiment where the two images are taken by the same scanner 2 at different times, "deformations" refers to portions of object 5 that have moved between the time of taking the first image and the time of taking the second image. In the case where object 5 is a human body 5, these deformations may correspond to shrinkage of tumors occasioned by the patient 5 having received radiation therapy, or to the movement of organs within the patient's body 5. In the case where object 5 is a human body undergoing radiation therapy, the first image is normally referred to as the reference image, and the second image is referred to as the registered image. In the alternative embodiment where the two images are taken at roughly the same time by two different scanners 2, the deformations correspond to differences in the images that are inherently caused by the different types of scanners 2. In the alternative embodiment where two different objects are scanned, one scan may be of a patient who is currently under treatment, said first scan being compared to a second scan of a previously treated patient having a similar disease.

Deformations are considered with respect to a scalar property. The scalar property can be the maximum deformation of a portion of object 5 without regard to the direction of the deformation. Alternatively, the scalar property can be the deformation of a portion of the object 5 along a preselected axis. In general, the scalar property can be the result of any mathematical operation that is applied to the vector field. When the results of the invention are displayed on display 6, as illustrated in FIGS. 3 through 7, three orthogonal axes are normally defined. The X and Y axes are orthogonal to each other and lie in the plane of the displayed image. The Z axis is orthogonal to each of the X and Y axes, i.e., it is orthogonal to the page in each of FIGS. 3 through 7.

The tabulating step 22 is performed by computer 4 by either calculating a deformation map that defines the deformations between the two images, or by using a deformation map that has been drawn manually by a person who has examined the two images. In that case, the manually-drawn deformation map is fed to computer 4 before computer 4 performs the tabulating step. The deformation map can comprise a vector field, one or more mathematical equations, and/or any mathematical representation that illustrates the deformations, such as a geometrical model.

In step 23, computer 4 quantizes a preselected (by the user) range 43, 53 of deformations into a set of discrete segments (quantization intervals). The number of quantization intervals is preselected by the user based upon the desired degree of differentiation in the resulting displays, the resolution of the imaging system, and/or other factors.

Figure 5:
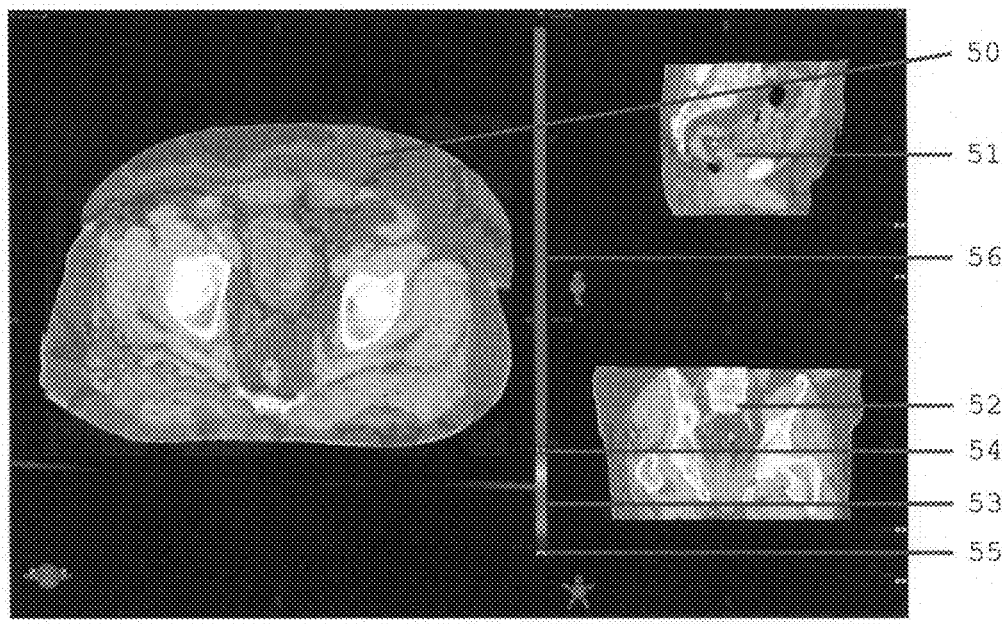
FIG. 5 is a screen shot showing results of a second embodiment of the present invention in which deformed images 50, 51, 52 are displayed along with superimposed color overlays.

In step 24, computer 4 assigns a unique color out of a discrete or quasi-continuous set of colors to each quantization interval, thereby producing a color overlay that is spatially aligned with the images when displayed on display 6. The expressions "quantization" and "quasi-continuous" are used, rather than simply "continuous", even in the case where the user has selected a continuous-color rainbow-like spectrum as illustrated in FIGS. 4 and 5, because computer 4 is normally a digital computer and therefore can store and process just a finite number of colors, not an infinite number of colors. In some embodiments, the range 43, 53 has a high cutoff 44, 54 and a low cutoff 45, 55. In one embodiment, as illustrated in FIG. 4, if a deformation is greater than the high cutoff 44, computer 4 assigns to such a deformation the color that it assigned to the high cutoff 44. Similarly, in some embodiments, if a deformation is less than the low cutoff 45, computer 4 assigns to such a deformation the color that it assigned to the low cutoff 45. Both of these cases are illustrated in FIG. 4. In other embodiments, such as illustrated in FIG. 5, when a deformation is greater than the high cutoff 54, computer 4 assigns to such a deformation transparency, i.e. the color overlay is made to be transparent. In certain embodiments, when the deformation is lower than the low cutoff 55, computer 4 also assigns to such a deformation transparency, as also illustrated in FIG. 5. Such an embodiment is particularly useful in the case where the lowest possible deformation lower than the lowest deformation of interest. The embodiments discussed in this paragraph can be mixed and matched, i.e., in some cases deformations that are greater than the high cutoff 44, 54 are assigned the color that computer 4 assigned to the high cutoff 44, 54, whereas deformations lower than the low cutoff 45, 55 are assigned transparency by computer 4.

In step 25, display 6, after receiving the requisite data from computer 4, simultaneously displays in spatial alignment the color overlay and a representation of at least one of the first and second images, thus making the deformations readily viewable in color. In one embodiment, the representation is a deformed image of one of the first and second images; typically, the representation is a deformed image of the first (reference) image. As used in this specification including claims, "deformed image" means that the image has been processed by applying the deformation map to the image. This embodiment is particularly useful when the users have done a lot of work ("painting") on the reference image, and don't want to have to repeat that work on the registered image when the comparison of the two images is being made. FIGS. 3 through 6 illustrate embodiments where a deformed reference image is used.

In another embodiment, a deformed image is not used, but rather both the reference image and the registered image are displayed, in addition to the color overlay, all in spatial alignment. This approach causes a more cluttered rendition than the previously described embodiment.

Figure 6:
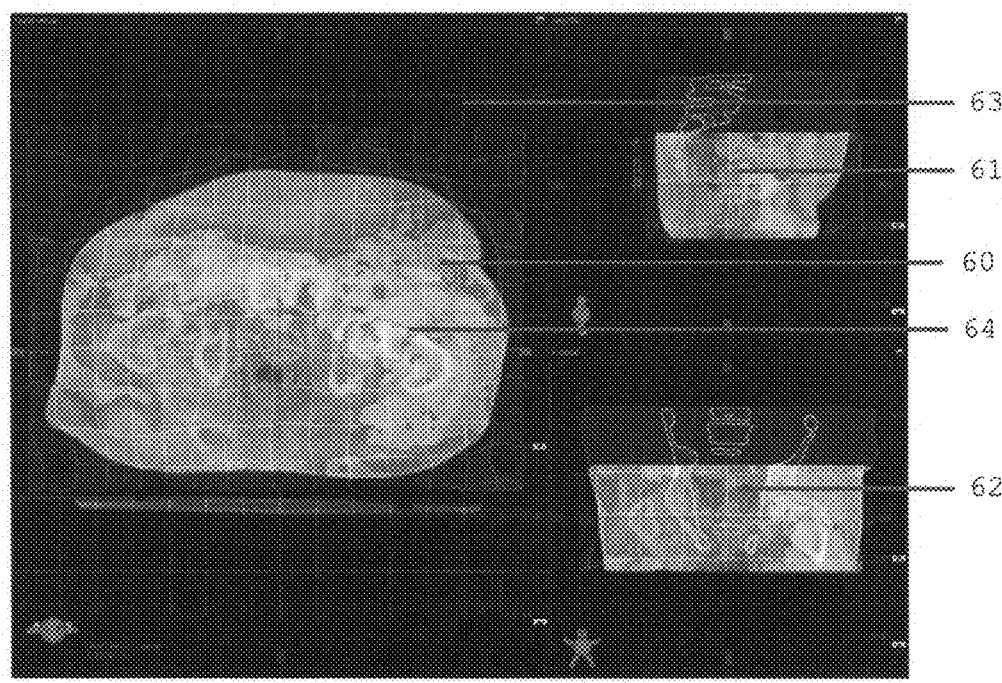
FIG. 6 is a screen shot showing results of a third embodiment of the present invention in which deformed images 60, 61, 62 are displayed along with superimposed color overlays, grid representations 63, and contours 64.

In some embodiments, the displaying step 25 further comprises simultaneously displaying a second overlay in addition to the color overlay and the representation. This is illustrated in FIG. 6, in which two additional overlays have been used: a grid representation 63 of the deformation field and a set of contours 64 representing regions of interest within the image (in this case, bone structures and borders of a patient's bladder and rectum). The contours 64 can be produced by computer 4 or drawn by hand by the user. In the grid representation 63, portions of the body 5 where there has been no deformation are portrayed as a series of interconnected squares. Where there has been deformation, the grid representation 63 shows the degree and direction of deformation. The second overlay can also comprise isocenters, beams, and/or coordinate axes.

In some embodiments, the object 5 is scanned in a series of thin slices 1(1) through 1(n) (see FIG. 1), and then the slices 1 are stacked representationally within computer 4 to form a three-dimensional volume representing the portion of interest within the object 5. In this case, the first and second images are each two-dimensional representations of the thin slices 1. This enables the displaying step 25 to display a plane of the object 5 other than (and at an arbitrary angle with respect to) a plane of the first image or the plane of the second image. This phenomenon is illustrated in FIGS. 3 through 6, in which screen shots 31, 32, 41, 42, 51, 52, 61, and 62 all lie in planes that are orthogonal to the planes of the first and second images, i.e. planes 30, 40, 50, and 60, respectively.

The invention can be implemented using techniques other than color to show the deformations. For example, rather than a range of colors, a varying range of grayscale or isolines can be used. In these embodiments, all of the previously described techniques can be used, except that the processing performed by the assigning step 24 and the displaying step 25 are somewhat different. In the assigning step 24, the computer 4 assigns a different level of gray to each quantization interval or isolines to specific scalar values, rather than colors. In the displaying step 25, the deformations are highlighted by varying grayscale or by different isolines, rather than by different colors.

FIG. 3 is a screen shot of display 6 illustrating deformed images 30, 31, and 32 that correspond to each other. Item 30 is a top planar view taken through the pelvis of a human 5. The little green men shown in FIGS. 3 through 6 indicate the orientation of the images with respect to each other. Thus, image 31 is a side view corresponding to image 30, and image 32 is a front view corresponding to image 30.

FIG. 4 shows images 40, 41, and 42, which are identical to images 30, 31, and 32, respectively, except that a color overlay has been applied to images 40, 41, and 42. Item 46 is a color bar showing all of the possible colors that can be displayed. The user has selected a color range 43 that has a red at its high cutoff 44 and blue at its low cutoff 45. The user has also selected the embodiment where deformations greater than the high cutoff 44 are assigned the same red by computer 4 as computer 4 assigned to deformations exactly at the high cutoff 44. Similarly, for deformations that are less than the low cutoff 45, computer 4 has assigned the same blue color that computer 4 has assigned to deformations that occur exactly at low cutoff 45.

FIG. 5 differs from FIG. 4 in two major respects. First of all, FIG. 4 shows deformations along the Z axis, whereas FIG. 5 shows deformation length regardless of the direction of the deformation. The second difference between the two Figures lies in the assignment of colors of deformations that are greater than the high cutoff 54 of the color range 53, and deformations that are less than the low cutoff 55 of the color range 53. In FIG. 5, item 56 is a color bar that shows all of the possible colors that can be displayed. Computer 4 has assigned a red color to deformations that are greater than high cutoff 54. Similarly, computer 4 has assigned transparency to deformations that are less than low cutoff 55. As stated previously, this technique is particularly useful in cases where the lowest possible deformations are zero but the most interesting deformations are greater than zero.

FIG. 6 illustrates deformed images 60, 61, and 62 that have been overlaid with not just a color overlay but with two additional overlays as well: grid representation 63 of the deformation field and contours 64, as previously described. Moreover, in FIG. 6, both the deformed reference image and the undeformed registered image are semi-transparently blended into each other.

Figure 7:
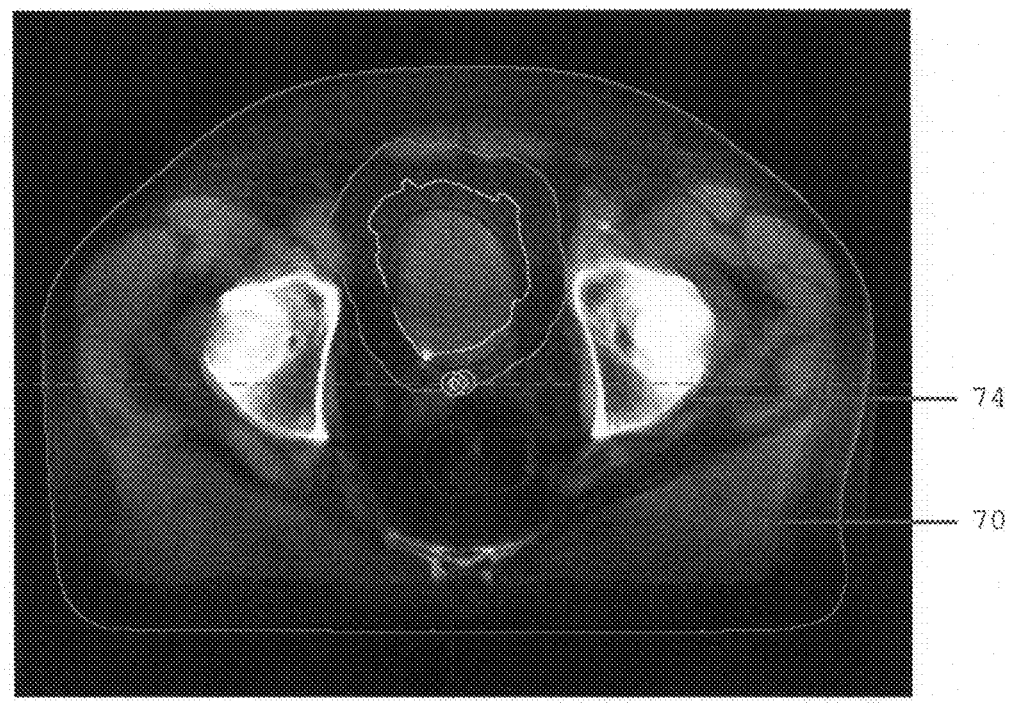
FIG. 7 is a screen shot showing results of a fourth embodiment of the present invention in which a non-deformed image using color A has been blended with a deformed image using color B.

FIG. 7 illustrates an alternative embodiment of the present invention in which a non-deformed image using a first color, in this case green, has been blended with the same but deformed image using a second color, in this case magenta. If two identical images (one using the green color channel, the other the magenta color channel) are combined, we get a gray image 70. But as soon as one of the images geometrically deviates from the other image (may be just locally), the result contains a certain amount of color 74, which depends on the deviation of the values of the two images at certain points in the drawing plane. So we do not need an additional contour overlay to get the colors that are shown in FIG. 7. The colors are an inherent result of the process.

The above description is included to illustrate the operation of the preferred embodiments, and is not meant to limit the scope of the invention. The scope of the invention is to be limited only by the following claims. From the above discussion, many variations will be apparent to one skilled in the art that would yet be encompassed by the spirit and scope of the prevent invention.

What is claimed is:
1. A computer-implemented method for graphically displaying representations of deformations, said deformations defined by comparing a first image of a view of a first scanned object with a second image of a view of a different scanned object, said method comprising the steps of:
   scanning the objects twice to produce the first and second images;
   tabulating deformations in a deformation map, comprising at least one three-dimensional vector, wherein each three-dimensional vector describes a geometrical change of a portion of the object when comparing said first and second images;
   converting said tabulated deformations into a corresponding set of scalar quantities over a preselected range;
   dividing the range into a set of discrete quantization intervals;
   assigning a unique color out of a discrete or quasi-continuous set of colors to each quantization interval to produce a color overlay, said color overlay showing the deformations; and simultaneously displaying the color overlay and a representation of at least one of the first and second images, whereby said deformations are shown in color; wherein:

the set of scalar quantities is converted from said tabulated deformations by determining at least one parameter from the group of parameters consisting of:

magnitude of at least one three-dimensional vector, and scalar value of one component of at least one three-dimensional vector.

2. A computer-implemented method for graphically displaying representations of deformations, said deformations defined by comparing a first image of an object with a second image of the same or a different object, said method comprising the steps of:

scanning the object(s) twice to produce the first and second images;

tabulating deformations in a deformation map, comprising at least one three-dimensional vector, wherein each three-dimensional vector describes a geometrical change of a portion of the object when comparing said first and second images;

converting said tabulated deformations into a corresponding set of scalar quantities over a preselected range;

dividing the range into a set of discrete quantization intervals;

assigning a unique color out of a discrete or quasi-continuous set of colors to each quantization interval to produce a color overlay, said color overlay showing the deformations; and simultaneously displaying the color overlay and a representation of at least one of the first and second images, whereby said deformations are shown in color; wherein:

the set of scalar quantities is converted from said tabulated deformations by determining at least one parameter from the group of parameters consisting of:

magnitude of at least one three-dimensional vector, and scalar value of one component of at least one three-dimensional vector;

the range has a high cutoff and a low cutoff; and deformations greater than the high cutoff and deformations lower than the low cutoff are represented by transparency.

* * * * *